United States Patent [19]
Godvigovna et al.

[11] Patent Number: 5,880,293
[45] Date of Patent: Mar. 9, 1999

[54] METHOD FOR CATALYTIC CONVERSION OF CARBON DIOXIDE

[75] Inventors: Tomilova Ralisa Godvigovna, Dolgoprudnyj; Ragulin Valerij Vladimirovich, Chernogolovka; Lermontov Sergej Andreevich, Chernogolovka; Shkavrov Sergej Vladimirovich, Chernogolovka; Chornykh Elena Vasilyevna, Dolgoprudnyj; Kurdyumova Nadezhda Rudolfovna, Chernogolovka; Zefirov Nikolaj Serafimovich, Moscow, all of Russian Federation

[73] Assignee: Iskra Industry Co., Inc., Tokyo, Japan

[21] Appl. No.: 961,144

[22] Filed: Oct. 30, 1997

[30] Foreign Application Priority Data

Oct. 31, 1996 [RU] Russian Federation ............. 96121458

[51] Int. Cl.$^6$ .................................................. C07D 317/08
[52] U.S. Cl. .............................................. 549/230
[58] Field of Search ............................................. 549/230

[56] References Cited

U.S. PATENT DOCUMENTS

| | | | |
|---|---|---|---|
| 2,773,070 | 12/1956 | Lichtenwalter et al. | 549/230 |
| 2,873,282 | 2/1959 | McClellan | 549/230 |
| 3,535,341 | 10/1970 | Emmons et al. | 549/230 |
| 4,663,467 | 5/1987 | Kruper, Jr. et al. | 549/229 |
| 4,786,741 | 11/1988 | Sachs | 549/230 |
| 4,892,954 | 1/1990 | Brindopke et al. | 549/229 |
| 4,981,948 | 1/1991 | Kawachi et al. | 528/405 |
| 4,982,954 | 1/1991 | Lazar | 272/93 |
| 5,283,356 | 2/1994 | Marquis et al. | 558/260 |
| 5,631,386 | 5/1997 | Gupta | 549/228 |

FOREIGN PATENT DOCUMENTS 0 297 647  11/1990  European Pat. Off. .

OTHER PUBLICATIONS

Kasuga et al. Cycloaddition of Carbon Dioxide to Propylene Oxide catalysed by Tetra–t–butylphthalocyaninatoaluminium (III) Chloride, Polyhedron, vol. 15, No. 1, pp. 69–72, 1996, Nov. 1995.

Kuninobu Kasuga et al., Cycloaddition of Carbon Dioxide . . ., vol. 69, No. 10, Oct. 1996 pp. 2885–2888; XP002055595.

Chemical Abstracts No. XP002055596, vol. 124, No. 9, 1996; K. Kasuga et al; Cycloaddition of Carbon Dioxide . . ., p. 1183.

Polyhedron, vol. 15, No. 1, 1996, JP, pp. 69–72.

*Primary Examiner*—John Kight
*Assistant Examiner*—Raymond Covington
*Attorney, Agent, or Firm*—Foley & Lardner

[57] ABSTRACT

A process for catalytic conversion of carbon dioxide by reacting it with an olefin oxide in the presence of a catalyst which is a tert-butyl-substituted phthalocyanine complex of a metal.

18 Claims, No Drawings

METHOD FOR CATALYTIC CONVERSION OF CARBON DIOXIDE

BACKGROUND OF INVENTION

1. Field of Invention

The invention concerns a process for the conversion of carbon dioxide by a reaction thereof with epoxide (olefin oxide) and a subsequent conversion to alkylenecarbonate. For the first time, tert-butyl-substituted mono- and diphthalocyanine complexes of metals are provided as catalysts for this process.

2. Related Art

The development of a process for conversion of carbon dioxide, the concentration of which, in the atmosphere, is increasing gradually, is urgently sought. A promising approach for removing carbon dioxide from its circulation is conversion thereof into ecologically safe polymers (for example, polypropylenecarbonates). Therefore the search for processes to synthesize initial monomer substances (in particular alkylenecarbonates) from carbon dioxide, for the purpose of subsequent converting the monomers into polymers, represents a rather urgent problem.

The reactions between alkylene oxides and carbon dioxide in the presence of catalysts are known: see U.S. Pat. Nos. 2,773,070; 2,873,282; 3,535,341; 4,786,741; European Patent No. 0 297 647; and Japanese Patent Publication No. 63-181765. As a rule, catalysts used in these reactions were halogen-containing compounds at a rather large concentration, the application of which results in formation of a large quantity of impurities. In addition, most catalysts previously proposed lose activity in the given reactions, or rather promote interaction between epoxide molecules, instead of with carbon dioxide. Therefore there is the requirement for catalysts which are not destroyed during the conversion of carbon dioxide, do not add impurities to products of reaction and allow effective assimilation of carbon dioxide resulting in a reduction in the environment.

The process closest to the present invention is a process for formating alkylenecarbonates using phthalocyanine complexes of metals as catalysts, described in the U.S. Pat. No. 5,283,356. A drawback of this method is the low solubility of the used catalysts, that results, apparently, in a heterogeneous progression of the process with very low efficiency. In addition, a reaction in heterogeneous conditions does not allow to reach quantitative conversion of carbon dioxide, and, accordingly, much reduces the efficiency of said process.

SUMMARY OF INVENTION

Accordingly, the present invention provides a process for the catalytic conversion of carbon dioxide by reacting it with an olefin oxide in the presence of a catalyst which is a tert-butyl-substituted phthalocyanine complex of a metal.

DETAILED DESCRIPTION

The applicant of the present invention has found that the specified drawback can be eliminated by using an alkyl-substituted phthalocyanine complexe of metal, whose solubility is higher, by several orders of magnitude, than the solubility of a corresponding unsubstututed analogue. For the purpose of finding new effective catalysts, tert-butyl-substituted phthalocyanine complexes of practically all metals in the periodic table were synthesized. The presence of such substituents on the ring structure in a phthalocyanine molecule results in sharp increases in solubility of complexes (by two times) in organic solvents and, hence, a homogeneous catalytic reaction can proceed. It is possible to reduce the necessary quantity of the catalyst and, more importantly, the homogeneous reaction provides quantitative (100%) conversion of carbon dioxide. Synthesis of alkylenecarbonate by an conversion of carbon dioxide in olefin oxide in the novel carbon dioxide conversion catalysist provides a quantitative carbon dioxide conversion as follows:

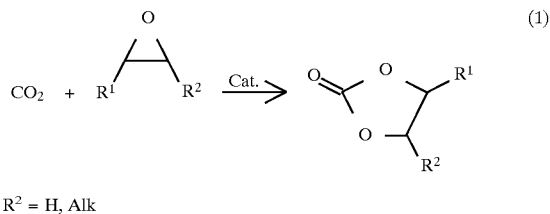

$R^1, R^2 = H, Alk$

The invention concerns a process of assimilating carbon dioxide by a reaction thereof with an olefin oxide followed by a subsequent conversion to alkylenecarbonates. As catalysts for this process, for the first time, tert-butyl-substituted mono- and diphthalocyanine complexes of metals are proposed.

Propylene oxide, ethylene oxide and epichlorohydrine were chosen as olefin oxides. To determine the yield of a product, a direct crystallization method was used. The reaction mixtures were subjected to vacuum distillation so as to obtain fractions representing individual compounds confirmed by IR- and NMR $^1$H-spectra. Ethylenecarbonate has a boiling point of 147°–149° C. (20 Torr), and propylenecarbonate has a boiling part of 152°–154° C. (20 Torr).

The reactions proceed at temperature from 100° to 250° C., however the quantitative yield can be achieved at a temperature of 180° C. Although the reaction can be observed at atmospheric pressure, the optimum condition is reached at pressure 50 Atm or above. The required pressure is reached by the introduction of a certain quantity of carbon dioxide. The reaction mixture is heated to certain temperature and maintained for a certain time at the given temperature and the chosen pressure.

Olefin oxides and carbon dioxide are mixed in a proportion, ensuring an excess of carbon dioxide in comparison with the stoichiometric quantity, required in reaction. The excess of carbon dioxide can be from 1.5 mol up to 20 mol for each mol of olefin oxides. It is necessary to avoid an excess of olefin oxide to avoid the formation of undesirable products of the olefin oxides polymerization and the creation of explosive conditions.

In the present invention, alkylsubstituted mono- and diphthalocyanine complexes of metals are provided as catalysts for carbon dioxide conversion.

Metalphthalocyanines are represented by the following formulas:

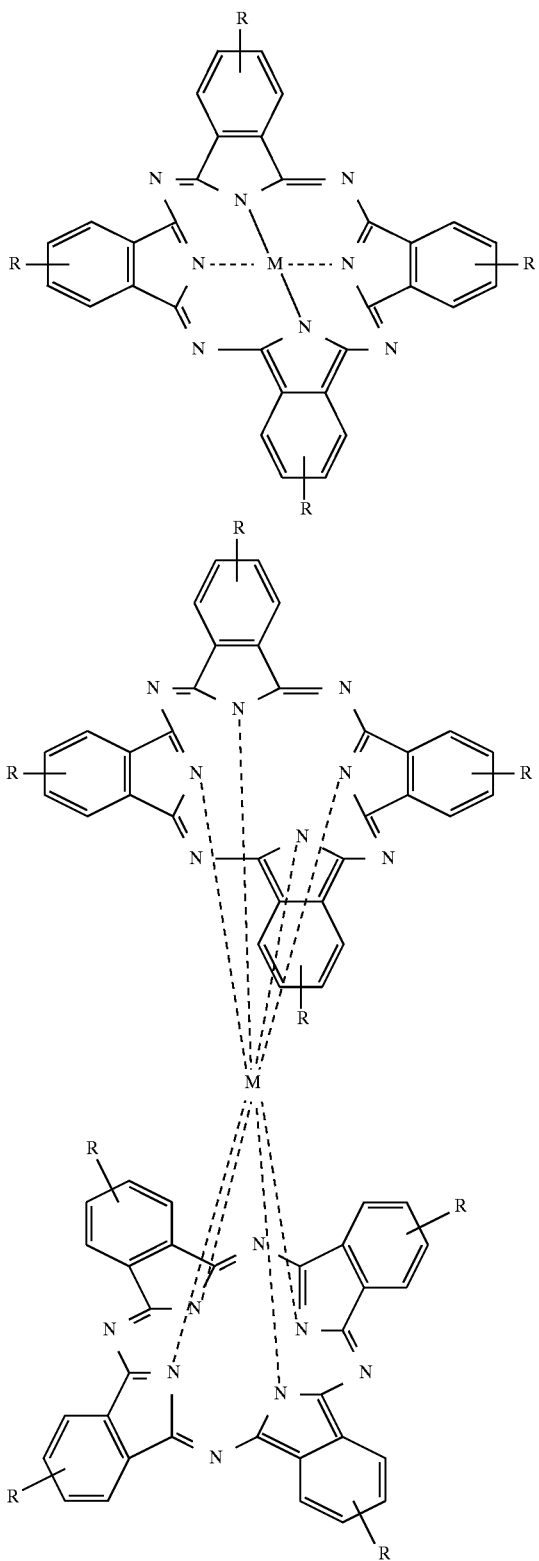

Wherein R is an alkyl and M is a 2-, 3- or 4-valent metal, such as aluminum, dysprosium, indiume, chromium etc.

A quantity of the catalyst used in the present process of carbon dioxide conversion is from 0.05 to 5.0% in relation to the olefin oxide weight. An increase in concentration of the catalyst results in a more complete and quick carbon dioxide conversion, all other things being equal.

It was found that tert-butyl-substituted phthalocyanine aluminum ($Pc^tAlCl$), at a quantity of 2.5% by weight of the propylene oxide, provides a quantitative yield of propylencarbonate, at 180° C. for 2 hours, according to the Scheme:

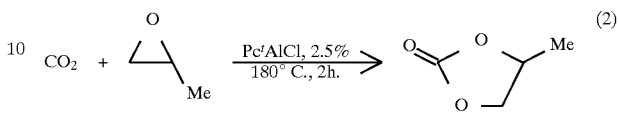

It appears that the increase of solubility of the catalyst, due to the introduction of the alkyl substituent in a molecule increases its efficiency and results in a quantitative yield of propylenecarbonate at a quantity of the catalyst about three times smaller than in the prototype.

The second possibility for enhancing the yield is based on an increase in the number of active centres of catalyst in a reaction mixture (apart from an increase of the catalyst solubility) arranged, by the present inventors, by coating the catalyst on the carrier. $SiO_2$, neutral $Al_2O_3$ and alkaline $Al_2O_3$ were tested as carriers. It appeared that the coating of the catalyst on $SiO_2$ and neutral $Al_2O_3$ did not give positive results, while the use of alkaline $Al_2O_3$ ($Al_2O_3/OH^-$) improved catalytic activity of the system. The catalyst was prepared by dissolving an appropriate substituted phthalocyanine complex of metal in $CH_2Cl_2$, adding a necessary quantity of $Al_2O_3/OH^-$ and evaporating this mixture in vacuum.

Unsubstituted phthalocyanine was coated by dissolving it in a large amount of acetone, coating the solution on $Al_2O_3/OH^-$ and then evaporating the solvent in a vacuum.

EXAMPLES

Examples described below illustrate the present invention but do not limit the scope of invention to the Examples.

Example 1

In a dry steel autoclave having a 100 ml capacity equipped with a valve, 62.5 mg of tert-butyl-substituted phthalocyanine aluminum and 2.5 g (44 mmol) of propylene oxide were placed. The autoclave was closed, and then filled with carbon dioxide up to a pressure of 50 Atm (110 mmol). The filled autoclave was shaken sometimes, heated to a temperature of 180° C. and was maintained at this temperature for 2 hours. After that, autoclave was cooled to room temperature, and the excess pressure was discharged through the valve. Then the reaction mixture was dissolved in $CH_2Cl_2$ to a volume of 15 ml and the solution was used in order to determine a degree of the reaction by IR-spectrometer. A target product was obtained in a pure state by evaporation in vacuum, and weighted. The yield of propylenecarbonate was about 100%.

Comparative Example 2

An experiment, similar to Example 1 except that 0.8 g of a unsubstituted phthalocyanine aluminum as the catalyst, 15 g (0.26 mol) of propylene oxide and 18.5 g (0.42 mol) $CO_2$ were used, was carried out. The yield of propylenecarbonate was 88.4%.

Example 3

An experiment, similar to Example 1 except that 0.25 g of tert-butyl-substituted phthalocyanine aluminum as the catalyst, 15 g (0.26 mol) of propylene oxide and 18.5 g (0.42 mol) of $CO_2$ were used, was carried out. The yield of propylenecarbonate was 92.1%.

Example 4

An experiment, similar to Example 1 except that 0.8 g of tert-butyl-substituted diphthalocyanine dysprosium as the catalyst, 15 g (0.26 mol) of propylene oxide and 18.5 g (0.42 mol) of $CO_2$ were used, was carried out. The yield of propylenecarbonate was 12.3%.

Example 5

An experiment, similar to Example 1 except that at 150° C., 0.4 g of tert-butyl-substituted phthalocyanine aluminum as the catalyst, 17.5 g (0.4 mol) of ethylene oxide and 35 g (0.8 mol) of $CO_2$ were used, was carried out. The yield of ethylenecarbonate was 25.4%.

Example 6.

An experiment, similar to Example 1 except that 0.8 g of tert-butyl-substituted phthalocyanine indium as the catalyst, 15 g (0.26 mol) of propylene oxide and 18.5 g (0.42 mol) of $CO_2$ were used, was carried out. The yield of propylenecarbonate was 43.6%.

Example 7

An experiment, similar to Example 1 except that 0.18 g of tert-butyl-substituted phthalocyanine chromium as the catalyst, 12.5 g (0.22 mol) of propylene oxide and 30 g of (0.67 mol) of $CO_2$ were used, was carried out. The yield of propylenecarbonate was 70%.

Example 8

An experiment, similar to Example 1 except that 0.08 g of tert-butyl-substituted phthalocyanine aluminum, as the catalyst, coated on 1 g of alkaline oxide of aluminum, 7.5 g (0.13 mol) of propylene oxide and 18.5 g (0.42 mol) of $CO_2$ were used, was carried out. The yield of propylenecarbonate was 98.8%.

Example 9

An experiment, similar to Example 1 except that 0.4 g of a unsubstituted phthalocyanine aluminum, as the catalyst, coated on 10 g of alkaline aluminum oxide, 15 g (0.26 mol) of propylene oxide and 18.5 g (0.42 mol) of $CO_2$ were used, was carried out. The yield of propylenecarbonate was 91.3%.

Example 10

An experiment, similar to Example 1 except that 0.4 g of tert-butyl-substituted phthalocyanine aluminum, as the catalyst, 18 g (0.2 mol) of epychlorohydrine and 17.5 g (0.4 mol) of $CO_2$ were used, was carried out. The yield of 3-chloropropylencarbonate (B.p. 177°–180° C. at 10 Torr) was 90.1%.

Example 11

An experiment, similar to Example 1 except that 0.4 g of tert-butyl-substituted phthalocyanine aluminum, as the catalyst, 18 g (0.2 mol) of epychlorohydrine and 170 g (3.9 mol) of $CO_2$ were used, was carried out. The yield of 3-chloropropylenecarbonate was 100%.

Other examples used various mono- and diphthalocyanine complexes of various metals and other epoxides.

Thus, the resulting data provide an effective process for carbon dioxide conversion by the interaction thereof with an olefin oxide followed by a subsequent conversion to alkylenecarbonates. For the first time, tert-butyl-substituted mono- and diphthalocyanine complexes of metals are provided as catalysts for this process.

In addition, the present invention provide a process for carbon dioxide conversion producing alkylenecarbonates which are excellent starting materials for the production of polymers and diols.

We claim:

1. A process for the catalytic conversion of carbon dioxide consisting essentially of reacting the carbon dioxide with an olefin oxide in the presence of a catalyst which is a tert-butyl-substituted phthalocyanine complex of a metal.

2. A process according to claim 1 wherein the catalyst is coated on a carrier.

3. A process according to claim 1 wherein the tert-butyl-substituted phthalocyanine complex of metal is a planar and sandwich-like derivative.

4. A process according to claim 1, wherein the process is carried out at temperature 100° to 250° C. and at a pressure from atmospheric up to 50 Atm or higher.

5. A process according to claim 1, wherein the concentration of the catalyst is from 0.05 up to 5.0% in relation to the weight of olefin oxide.

6. A process according to claim 2 wherein the tert-butyl-substituted phthalocyanine complex of metal is a planar and sandwich-like derivative.

7. A process according to claim 2, wherein the process is carried out at temperature 100° to 250° C. and at a pressure from atmospheric up to 50 Atm or higher.

8. A process according to claim 3, wherein the process is carried out at temperature 100° to 250° C. and at a pressure from atmospheric up to 50 Atm or higher.

9. A process according to claim 2, wherein the concentration of the catalyst is from 0.05 up to 5.0% in relation to the weight of olefin oxide.

10. A process according to claim 3, wherein the concentration of the catalyst is from 0.05 up to 5.0% in relation to the weight of olefin oxide.

11. A process according to claim 4, wherein the concentration of the catalyst is from 0.05 up to 5.0% in relation to the weight of olefin oxide.

12. A process according to claim 1, wherein the olefin oxide is selected from the group consisting of propylene oxide, ethylene oxide, and epichlorohydrine.

13. A process according to claim 1, wherein the carbon dioxide and olefin oxide are initially mixed such that there is an excess of carbon dioxide in comparison with the stoichiometric quantity required for the reaction.

14. A process according to claim 1 wherein the catalyst comprises a tert-butyl substituted monophthalocyanine complex of a metal.

15. A process according to claim 1 wherein the catalyst comprises a tert-butyl substituted diphthalocyanine complex of a metal.

16. A process according to claim 1, which is carried out at a temperature of 100° to 250° C.

17. A process according to claim 1, which is carried out at atmospheric pressure.

18. A process according to claim 1, which is carried out at a pressure of 50 atmospheres or higher.

* * * * *